United States Patent [19]

Barnaby

[11] Patent Number: 4,734,649
[45] Date of Patent: Mar. 29, 1988

[54] APPARATUS FOR MEASURING THE RESISTIVITY OF A SAMPLE

[75] Inventor: Harold T. Barnaby, Duncanville, Tex.

[73] Assignee: Western Atlas International, Inc., Houston, Tex.

[21] Appl. No.: 837,811

[22] Filed: Mar. 10, 1986

[51] Int. Cl.$^4$ .................... G01N 27/04; G01R 27/08
[52] U.S. Cl. ........................................ 324/376; 324/64
[58] Field of Search ................................. 324/376, 64

[56] References Cited

U.S. PATENT DOCUMENTS 2,802,172  8/1957  Mueller et al. .................. 324/376
3,302,101  1/1967  Glanville ......................... 324/376
3,617,868  11/1971 Bietel et al. ..................... 324/376

Primary Examiner—Reinhard J. Eisenzopf
Assistant Examiner—Walter E. Snow
Attorney, Agent, or Firm—William A. Knox; Barry C. Kane

[57] ABSTRACT

A core holder is provided for making petrophysical measurements of core samples from a borehole. The core holder is designed to make resistivity measurements and fluid-flow tests under reproduced conditions of in-situ fluid saturation, reservoir pressure and reservoir temperature.

13 Claims, 13 Drawing Figures

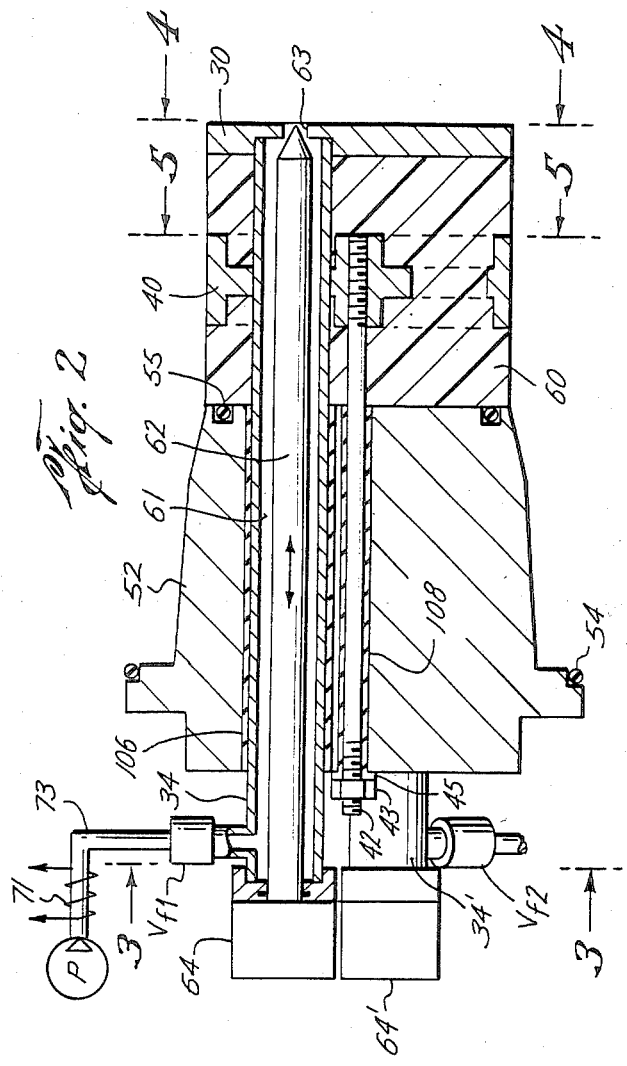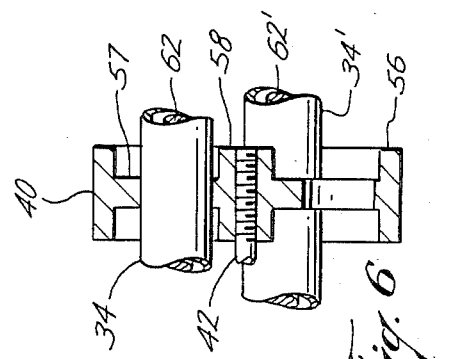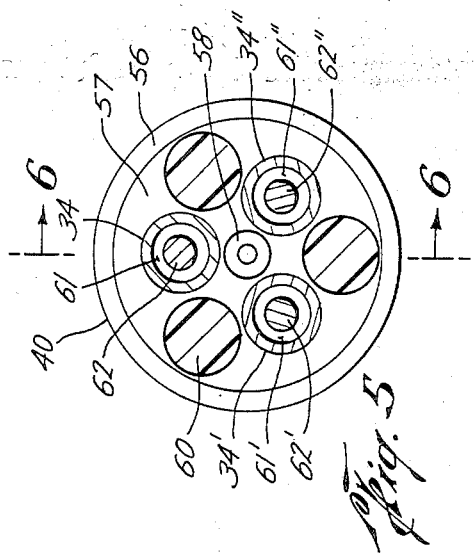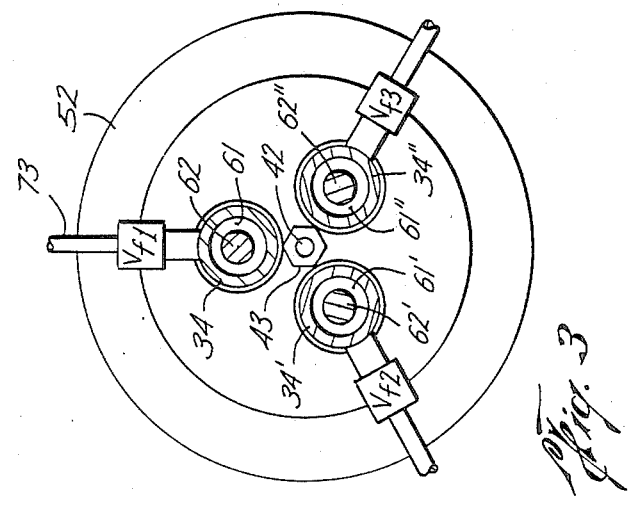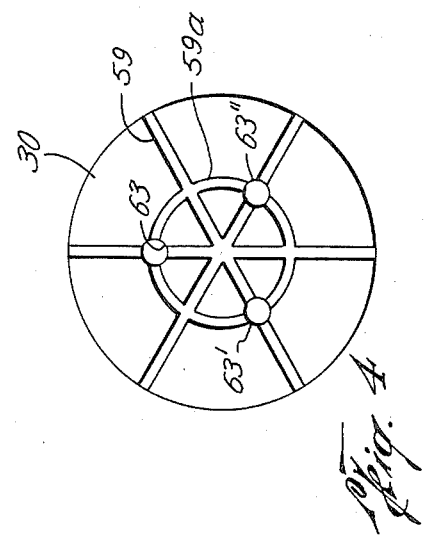

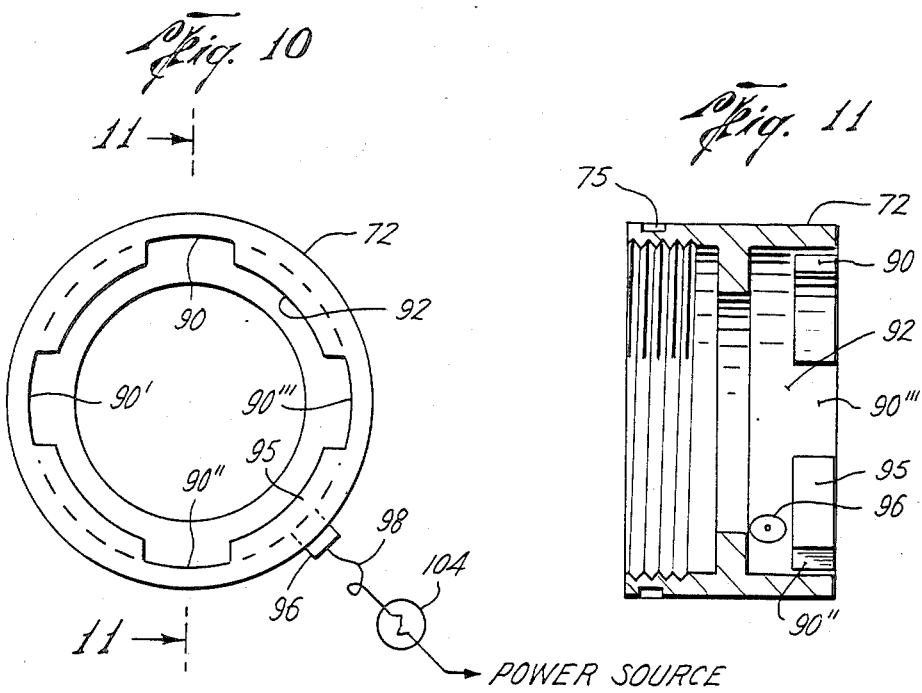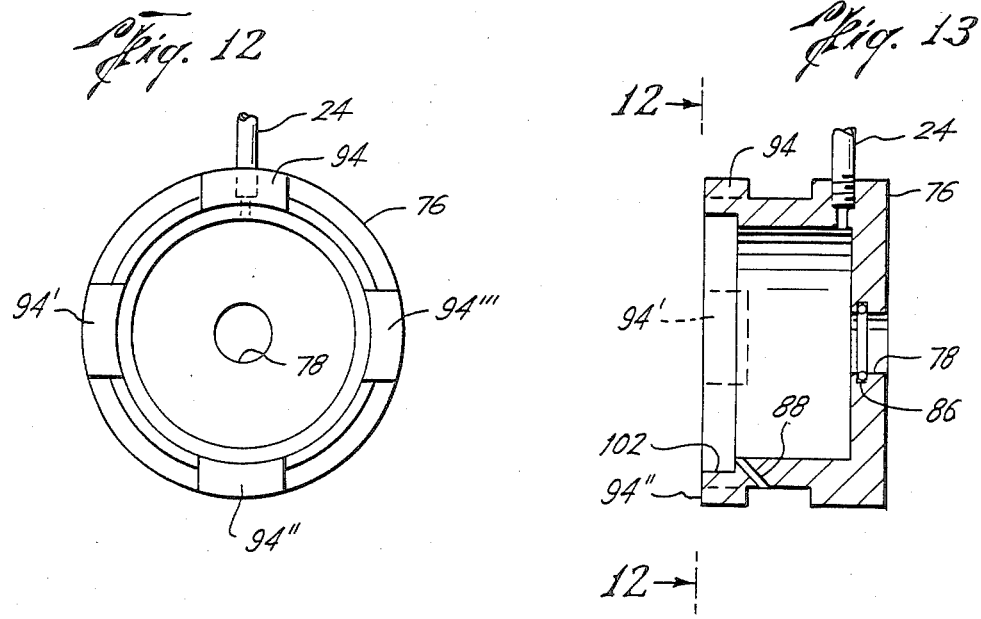

APPARATUS FOR MEASURING THE RESISTIVITY OF A SAMPLE

FIELD OF THE INVENTION

This invention is concerned with a holder for rock sample cores whose electrical resistivity is to be measured, for laboratory use.

BACKGROUND OF THE INVENTION

Geophysical exploration methods for metallic minerals, water-bearing strata, hydrocarbon deposits and for engineering applications, may include electrical resistivity surveys. In such a survey, employing a quadripole configuration, a pair of current electrodes are planted in the ground, spaced apart by several tens of meters. A pair of spaced-apart voltage electrodes are established in the ground between the two current electrodes. An electrical current is applied to the two current electrodes for a period of time such as several seconds or several tens of seconds and is then abruptly switched off. During application of the current, a voltage difference will be observed across the voltage electrodes. When the current is cut off, the voltage difference as seen at the voltage electrodes will slowly decay over several seconds. The decay time is a measure of the resistivity of the earth. The above technique, known as the Induced Potential (IP) method may be applied horizontally over the ground surface, or vertically, in a borehole. The simplistic explanation given above is subject to many variations such as different electrode arrangements, electrical measurement techniques and the like, depending upon the type of information sought, degree of sophistication required, and overall cost of the survey.

In order to interpret the results of an IP survey or of any other type of electrical prospecting, it is necessary to study, in the laboratory the petrophysical characteristics of typical rock-type specimens. Of interest are such matters as resistivity per unit volume of a rock in terms of porosity, mineral content, permeability, formation pressure, temperature and fluid content. Changes in the electrical properties of reservoir rock are indicative of either a physical change to the rock structure from overburden stress, resulting from pore pressure depletion, or changes in the composition of saturating fluids. Resistivity measurements can be a useful tool for production as well as exploration.

For laboratory tests, typically, the porous rock specimen is in the form of a cylindrical core an inch or two in diameter and a few inches long. The core is inserted into an insulating core barrel such as plastic, rubber or other insulating material. The two end faces are contacted by the current electrodes, usually via a brine solution that saturates the pore space. Silver/silver chloride (Ag/AgCl) voltage electrodes contact the core between the current electrodes to read the potential difference across a unit length of the core to measure the resistivity. It is preferable to mount the voltage electrodes well inside the current electrodes to avoid polarization effects that may distort the measurements.

One such laboratory device is described in a paper by Vinegar and Waxman in *Geophysics* V49, n8, August 1984, pp. 1267–1287. A tutorial monograph *Experimental and Theoretical Aspects of Induced Polarization* by J. Bertin and J. Loeb is published by Geopublication Associates and Gebrueder Barntraeger of Berlin, West Germany.

When studying core samples from boreholes, it is desirable to reproduce the in-situ conditions of reservoir pressure and temperature. In particular, laboratory equipment capable of simulating an overburden equivalent to a 20,000-foot or more depth is not believed to be presently available. Most such equipment provides resistivity measurements at a pressure not much greater than ambient atmospheric pressure. It is the purpose of this invention to provide a core barrel for use in making resistivity measurements of core specimens at great overpressures of at least 10,000 psi (pounds per square inch) with means for injecting selected interstitial fluids representative of various reservoir cconditions in the borehole.

SUMMARY OF THE INVENTION

The core holder of this invention is for use in measuring the resistivity of a rock core sample. Typically, the sample is cylindrical, having flat end faces. The core holder consists of a hollow outer tube or barrel that has inner and outer wall surfaces. A flexible sleeve, preferably of Buna rubber, is mounted inside the barrel for receiving core samples. The sleeve includes inner and outer wall surfaces. First and second voltage electrodes, having contact fingers, are embedded in the wall of the flexible sleeve with the exposed tips of the contact fingers flush with the inner wall surface of the sleeve. Upstream and downstream end cap assemblies seal the flexible sleeve against the ends of the outer barrel. First and second current electrodes are provided, designed to contact the end faces of a core sample received by the flexible sleeve, to pass an electrical current through the core. Voltage collector rings are insulated from and concentrically mounted outboard of the current electrodes. The voltage electrodes are arranged to straddle the current electrodes, to encircle the received core sample and voltage collector rings thereby to electrically couple the core sample with the corresponding voltage collector rings. Connecting passageways including valve means are provided to axially and laterally load the received core sample to simulate the in-situ overburden pressure to which the core sample was originally subjected. Means for reservoir temperature simulation is provided. Fluid-flow tests may be conducted.

BRIEF DESCRIPTION OF THE DRAWINGS

The advantages and benefits of this invention will best be understood by reference to the detailed description and to the drawings, wherein:

FIG. 2 is an enlarged cross section of the upstream end cap assembly;

FIG. 3 is an end view of FIG. 2 along section 3—3';

FIG. 4 is an end view of a current electrode along 4—4';

FIG. 5 is a view of voltage collector ring along section 5—5';

FIG. 6 is a cross section of FIG. 5 across section 6—6';

FIG. 10 is an end view of the downstream end cap;

FIG. 11 is a cross section of FIG. 10 along 11—11';

FIG. 12 is a cross-sectional view of the axial loading cylinder; and

FIG. 13 is an end view of FIG. 12 as seen from 13—13';

DETAILED DESCRIPTION OF THE PREFERRED EMBODIMENT

Figure 1:
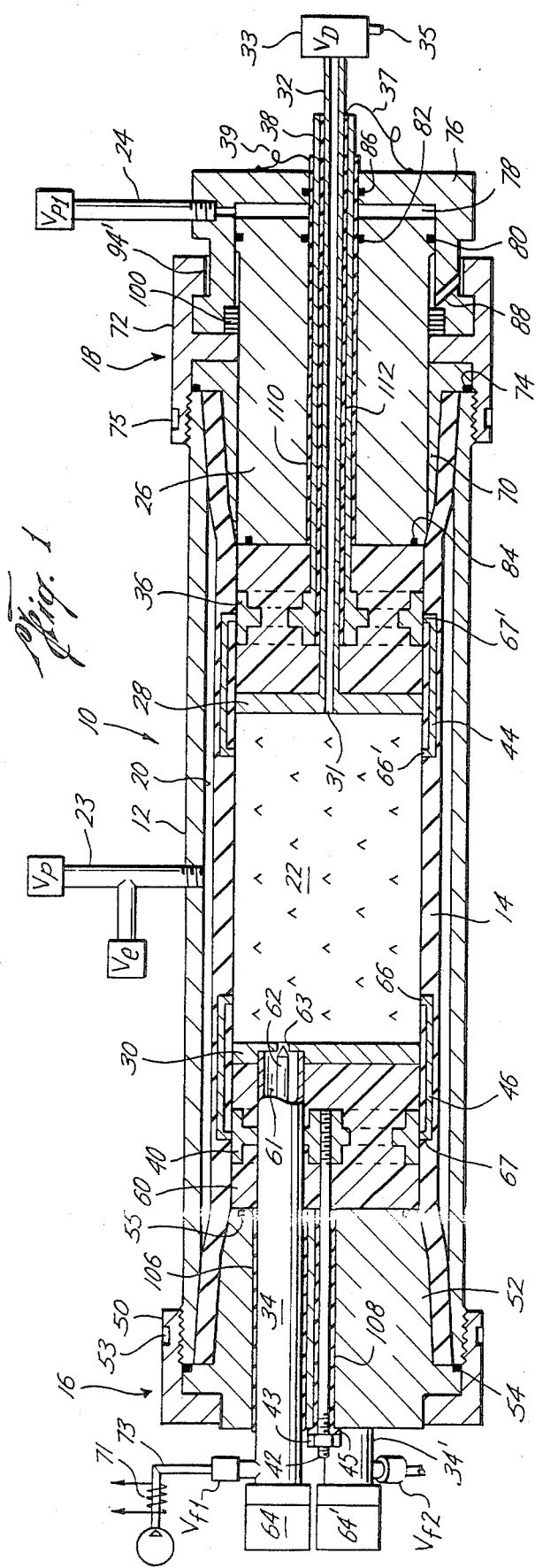
FIG. 1 is an overall sectional view of the quadripole resistivity-measuring device of this invention.
Figure 9:
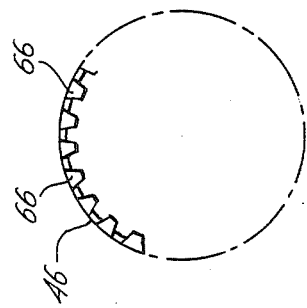
FIG. 9 shows the voltage electrode in its cylindrical form.
Figure 8:
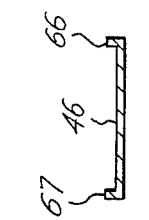
FIG. 8 is a side view of FIG. 7.

Referring now to FIG. 1, there is shown a quadripole rock-core holder 10 for making resistivity measurements of core samples in the laboratory. Means are provided for simulating in-situ conditions of overburden pressure and for saturating the rock sample with selected interstitial fluids, such as brine, in various concentrations that may be representative of the original connate fluids.

Core holder 10 consists of an outer barrel 12 which may be made of stainless steel with a wall thickness sufficient to withstand safely a pressure of at least 10,000 psi. Inside barrel 12, there is mounted a flexible Buna-rubber core-receiving sleeve 14 which is sealed in place at each end by upstream end cap assembly 16 and downstream end cap assembly 18. The outside diameter of sleeve 14 is sufficiently less than the inner diameter of barrel 12, to provide an annular chamber 20 therebetween. Pressure and exhaust valves Vp and Ve are in fluid communication with annular chamber 20. The purpose of exhaust valve Ve is two-fold: (1) to apply a vacuum to annular chamber 20, thereby to outwardly expand sleeve 14 so that a rock core sample such as 22 can be inserted therein and (2) to provide means for releasing high-pressure fluid from annular chamber 20 following a test run. Valve Vp, of course, is used to apply fluidic pressure, which preferably may be pneumatic, to laterally load the core sample 22 to simulate the overburden pressure. After the core sample 22 has been received by the sleeve 14, downstream end plug assembly consisting of major components 28, 36, 26, 32, 38, 39 and 76 are locked in place in downstream end cap 18. Fluidic pressure, either pneumatic or hydraulic, is applied through valve Vpl, line 24 to piston 26 which causes a current electrode 28 to axially load core sample 22 received by sleeve 14.

An electrical current is applied across core sample 22 by annealed silver current electrodes 28 and 30. Electrodes 28 and 30 are respectively coupled to an external current source (not shown) by hollow rod 32 and tube 34.

Insulated from current electrode 28, a voltage collector ring 36, is mounted outboard of and concentrically with the current electrode and is coupled to suitable external voltage measuring circuitry (not shown) by voltage conductor tube 38. Similarly, voltage collector ring 40 at the left, upstream end is insulated from and mounted outboard of, concentrically with current electrode 30, and is coupled to the measuring circuitry by voltage conductor rod 42. Voltage electrodes 44 and 46 are embedded in the wall of flexible core-receiving sleeve 14 to encircle and make contact between core sample 22 and voltage collector rings 36 and 40. The exposed tips of the contact fingers at the two bent-over sides of the voltage electrodes are flush with the inner wall surface of sleeve 14 so that firm electrical contact is made between the periphery of the core sample and the collector rings. The voltage electrodes straddle the current electrodes and are electrically isolated from them by the rubber sleeve. The voltage-electrode contact points, contacting the core, must lie inboard of the current electrode to avoid certain undesirable polarization effects that plagued previously-known core holders. It has been determined empirically that the spacing between a current electrode and a voltage electrode contact point should be at least ¼ inch. The term "near the end of the core" is defined to mean a point at least ¼ inch inboard from the end face of the core sample.

It is to be observed that hollow rod 32 is separated from tube 38 by insulation and shielding 112 of any desired type. Tube 38, in turn, is shielded from the metallic parts of end cap assembly 18 by insulation and shielding 110. The shielding may be grounded by leads 37 and 39 to prevent cross feed between voltage and current electrodes. Tube 34 and rod 42 at the upstream end cap assembly are similarly insulated.

In operation, very briefly, a core sample is placed inside sleeve 14 and is saturated with a fluid such as brine having a selected concentration. A current is applied across the ends of the core by the current electrodes. The voltage drop across the core between the two voltage electrodes is measured. From Ohm's law, the resistivity is computed. Either the time-domain or the frequency-domain induced potential method or any other suitable technique may be used. This invention is not limited to any particular experimental method of measurement.

The overall function and design of the core holder 10 has been outlined. For a better understanding of the device, the separate parts and assemblies will now be described in detail.

Upstream end cap assembly 16 is held in place by end cap locking ring 50. Locking ring 50 is screwed to barrel 12 and holds end plug 52 securely in place against the tapered end of sleeve 14. Holes, such as 53, are provided with which a spanner may be engaged. Refer now to FIG. 2, which is an enlarged view of end plug 52 in FIG. 1, including current electrode 30, current conductor tube 34, voltage collector ring 40 and voltage conductor rod 42. End plug 52 defines a central hole to receive voltage rod 42 and three additional holes centered at 120 degree intervals, as shown in FIG. 3, only one of which holes is shown in FIG. 2, for clarity. Suitable O-rings 54 and 55 are provided for sealing purposes.

Voltage collector ring 40 is shown in FIGS. 5 and 6. It consists of a stainless steel rim 56 coupled by webbing 57 to a hub 58. A plurality of apertures are cut into the webbing 57 as shown in FIG. 5. Three of the apertures are designed to receive the three tubes 34, 34', 34" shown in FIG. 3. Each side of voltage contact ring 40 is encapsulated with an insulating fiber-glass-filled epoxy mixture 60 as shown in FIG. 2. The three holes in webbing 57, not occupied by tubes 34, 34' and 34", provide communication between the two sides of the web of voltage collector ring 40 so that the epoxy mixture will form a homogenous structure through and around collector ring 40. The structure of voltage collector ring 36 is substantially the same as that of collector ring 40.

Current electrode 30 is a 10-gauge annealed silver disc. On the front face of the disc, as in FIG. 4, radial grooves such as 59 and grooved concentric rings such as 59a are cut. At three locations, 120 degrees apart, holes are drilled from the back side of the current electrode, to provide orifices 63,63',63" about 1/16 inch in diameter on the front face of the disc. Tube 34 is silver-soldered to the back of the disc 30 as shown in FIG. 2. The other two tubes 34' and 34" are similarly mounted.

A valve rod 62 having a tapered end is mounted inside tube 34 in a normally closed position against orifice 63. A control actuator 64, such as a spring-loaded solenoid, mounted on the end of tube 34, upon command, retracts valve rod 62 to open orifice 63. Fluid valve Vf1, in communication with the annulus 61 between valve rod 63 and the inner wall of tube 34 is provided to admit a flow of a first selected fluid such as brine. When valve rod 62 is retracted by control actuator 64, the fluid is allowed to flow into sleeve 14 through orifice 63 to saturate the core sample. The radial and concentric grooves on the face of current electrode 30 provide means for uniformly distributing the fluid over the exposed end face of the core sample. The selected fluid may be pressurized to reproduce the reservoir pore pressure. For that purpose, a suitable pump P may be employed. To reproduce reservoir temperature conditions on electrical heating coil 71, for example, may be used to heat the pressurized fluid as it passes through pipe line 73 to valve Vf1. A similar arrangement could be arranged for valve Vf2. The valve Vf2 associated with tube 34″ is used to admit a second different fluid such as brine at a different concentration, or oil. Valve Vfe coupled to tube 34′ may be used as a fluid exhaust valve for purging the first fluid so that a second fluid may be admitted. Control actuator 64 may be electrically, pneumatically or hydraulically operated.

Tube 34, in addition to providing means for admitting fluid to core sample 22 is also used as a current conductor to deliver current from an external source to current electrode 30. Tube 34 is, of course, insulated from end plug 52 by insulated tubing 106 of any desired type. The fiber-glass-filled epoxy module 60 insulates tube 34 from voltage contact ring 40.

Voltage conductor rod 42 is threaded into the hub 58 of voltage contact ring 40. Rod 42 is insulated from end plug 52 by suitable plastic tubing 108. Rod 42 as well as the voltage contact ring 40 is held in place by nut 43, beneath which is mounted an insulating washer 45.

Figure 7:
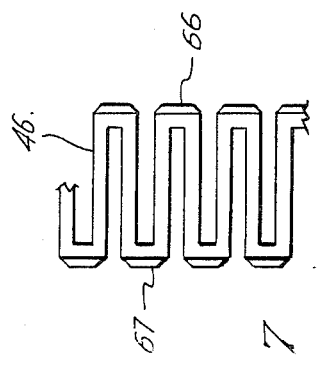
FIG. 7 is a flattened-out view of a voltage electrode.

Let us now refer to FIGS. 1 and 7–9 with respect to voltage electrodes 44 and 46 which are identical. Voltage electrode 46 is initially made from a slotted strip of 26-gauge silver sheet as shown in FIG. 7. The sides of the strip form laterally spaced-apart tapered fingers such as 66 and 67 which are bent at a right angle to the plane of the strip as in FIG. 8. The entire slotted strip 46 is then shaped around a mandrel to form a slotted cylinder as in FIG. 9, with inwardly, radially-disposed fingers 66. The slotted cylinders 44 and 46 are then suitably spaced apart and molded into the wall of flexible core-receiving sleeve 14 in a conventional manner but with the inside tips of fingers 66 and 67 exposed flush with the inner wall surface of sleeve 14. Voltage electrodes 44 and 46 constitute means for electrically coupling the core sample 22 with the voltage collector rings 36 and 40 by straddling current electrodes 28 and 30. When pressure is applied to annular chamber 20, fingers 66 make firm contact with the core sample near the end thereof, and fingers 67 make contact with the voltage collector rings.

Downstream end cap assembly 18, FIG. 1, includes a downstream ferrule 70 for holding sleeve 14 in place. A threaded end cap 72 seals ferrule 70 in place against the downstream end of barrel 12. An O-ring 74 is provided for sealing. Cavities, such as 75, are provided for engagement by a spanner. Axial loading cylinder 78 and axial loading piston 26 together form means for axially loading core sample 22 when fluidic pressure is applied to chamber 78 through valve Vpl, of any desired type. The pressurized fluid may be pneumatic or hydraulic. The applied fluidic pressure is preferably about 10–15 psi greater than the lateral loading pressure applied through valve Vp and line 23. Suitable O-ring seals 80,82,84,86 prevent fluid leakage around piston 26, axial loading cylinder 76 and voltage electrode 38. Axial loading cylinder 76 includes a vent 88 for relieving pressure changes due to displacement of piston 26.

The downstream current electrode 28 is similar to current electrode 30 except that there is a central orifice 31 in the electrode that communicates with a passageway in hollow current rod 32. A drain valve Vd is secured to the end of hollow rod 32 to allow fluid flow from the core 22 to drain 35. By that means, fluid admitted from upstream valve Vf1 may be flushed through core 22 and out through Valve Vd, or the core may be desaturated after testing. Hollow current rod 32 couples current electrode 28 to an external power source (not shown). The structure of voltage collector ring 36 is the same as collector ring 40 except that collector ring 36 is coupled to an external voltage-measuring device by voltage conductor tube 38 which is welded to the hub of collector ring 36.

Axial loading cylinder 76 engages threaded end cap 72 by means of a breechlock-type locking mechanism as illustrated in FIGS. 10–13. End cap 72, on its outside face, includes four female quasi-rectangular apertures 90, 90′, 90″, 90‴ positioned around a central circular opening 92. The regions between the quasi-rectangular apertures thus form four retaining flanges such as 95. Axial loading cylinder 76 has, on its inner face, four male fingers 94, 94′, 94″, 94‴ which fit into the corresponding female apertures on end cap 72. The two parts, 72 and 76 then lock in place when axial loading cylinder 76 is rotated 45 degrees counter-clockwise. An electrical contact 96 is threaded into the side of one of the retaining flanges 95. When axial loading cylinder 76 is locked into place by counter-clockwise rotation, finger 94″ engages contact 96 to close an electrical circuit 98. Circuit 98 is interconnected with a warning light 104 to indicate that the breechlock is secure. Afternatively it could be interconnected with the ancillary equipment associated with core holder 10 (not shown) that provides fluidic pressure through the respective pressure valves. Unless axial loading cylinder is in place and locked, none of the equipment can be turned on. That function serves as a safety feature. The breechlock locking mechanism is described by way of example in terms of four fingers and apertures but more or fewer could be used. A plurality of plastic washers 100 are fitted into an enlarged portion 102 of axial loading cylinder 76 to create a bearing for piston 26. It should be understood that contact 96 could be repositioned on flange 95 so that clockwise rotation of cylinder 76 would be possible.

In operation, end cap assembly 16, ferrule 70 and end cap 72 are installed in position to seal sleeve 14 to barrel 12 on a more or less permanent basis. That portion of end cap assembly 18 that includes current electrode 28, voltage contact ring 36 (the electrode assembly), axial loading cylinder 76 and axial loading piston 26 (axial loading assembly) are removed as a unit. Annular chamber 20 is evacuated through valve Ve to expand sleeve 14 against the inner wall of barrel 12. A core sample is then inserted into and received by sleeve 14. The axial loading cylinder assembly and the associated contact assembly are inserted through end cap 72 and locked into place. Fluidic pressure is applied to annular chamber 20 and to chamber 78 to laterally and axially load the core sample received by sleeve 14. The applied pressure simulates the actual in-situ overburden pressure. A selected fluid such as brine is now applied through one of the valves Vf1 or Vf2 to saturate core 22 to a pressure approaching the reservoir pore pressure. Drain valve Vd may be opened to allow free flow through the core and to conduct fluid-flow tests for permeability measurements. Electrical resistivity tests are then made as previously described. At the end of the tests, the applied pressures are relieved through the various exhaust and drain valves.

This invention has been disclosed with a certain degree of specificity by way of example but not by way of limitation. Many design details may be altered by those skilled in the art but which would be included in the scope and spirit of this invention which is limited only by the appended claims for example, O-rings 82 and 86 could be replaced by suitable packing glands. The core holder is shown as being cylindrical but it could be any other shape. An oven for the core holder could be provided for making measurements at in-situ temperatures.

I claim as my invention:

1. An apparatus for measuring the resistivity of a sample having opposite end faces, comprising:
   a barrel having an inner wall surface;
   a flexible sleeve mounted within said barrel, said flexible sleeve having inner and outer wall surfaces, said flexible sleeve defining an annular chamber between the inner wall surface of said barrel and the outer surface of said flexible sleeve;
   upstream and downstream end-cap assembly means for sealing said flexible sleeve against said barrel;
   a first and a second current electrode for electrically contacting the opposite end faces of said sample received by said flexible sleeve;
   a first and a second voltage collector, insulated from said first and second current electrode, mounted outboard of and concentric with said first and second current electrode;
   a first and a second voltage electrode embedded in said flexible sleeve, in spaced-apart relationship, said first and second voltage electrode having laterally spaced-apart contacts arranged flush with the inner wall surface of said flexible sleeve, the spaced apart contacts of each said voltage electrode straddling said first and second current electrode, encircling and contacting the received sample and said first and second voltage collector for electrically coupling said sample with said first and second voltage collector, respectively; and
   means for axially and laterally loading said received sample.

2. The apparatus as defined by claim 1, wherein the contacts of each of said voltage electrodes encircle the received sample inboard of and near opposite ends thereof.

3. The apparatus as defined by claim 1, wherein said upstream end cap assembly comprises:
   means for admitting at least a first selected fluid under pressure through said first current electrode.

4. The apparatus as defined by claim 1, further comprising:
   means contained within said downstream end cap assembly for applying an axial load, simulating an in-situ overburden pressure to said sample.

5. The apparatus as defined by claim 1, further comprising:
   first valve means mounted in said barrel in fluid communication with said defined annular chamber to expand said flexible sleeve; and
   second valve means mounted in said barrel in fluid communication with said annular chamber for laterally loading said sample with a desired fluidic pressure, simulating an in-situ overburden pressure.

6. The apparatus as defined by claim 1, wherein said current and voltage electrodes are fabricated from annealed silver for minimizing polarization effects between the electrodes.

7. The apparatus, as defined by claim 1, wherein said downstream end cap assembly comprises:
   axial-loading and electrode assemblies;
   an end cap;
   a breechlock means for engaging said axial-loading and electrode assemblies with said end cap; and
   an electrical contact for providing an indication when said breechlock means is secure.

8. The apparatus as defined by claim 3, comprising:
   means for flushing from said sample said first fluid through said second current electrode; and
   means for subsequently admitting a second fluid through said first current electrode.

9. The apparatus as defined by claim 3, further comprising:
   means for heating said first fluid to a temperature that reproduces an in-situ reservoir condition.

10. An apparatus for measuring the petrophysical characteristics of a sample recovered from a borehole, said sample having been subjected to in-situ reservoir conditions of temperature and pressure, comprising:
    a barrel;
    a flexible sleeve mounted in said barrel, said sleeve being sealed to said barrel at the ends thereof;
    current-electrode means for applying a current through a sample received by said flexible sleeve;
    voltage-electrode means, axially disposed exterior of said current-electrode means, for sensing a potential difference across the received sample due to application of a current therethrough, said voltage-electrode means also being embedded in said sleeve and insulated from said current-electrode means and adapted to extend inboard and around said current-electrode means and engage the received sample;
    means for simulating in said apparatus the in-situ reservoir conditions of interstitial fluid saturation, pressure and temperature to which said sample was originally subjected.

11. The apparatus as defined by claim 10, further comprising:
    means for axially and laterally loading said received sample to a pressure that simulates the in-situ overburden pressure.

12. The apparatus as defined by claim 10, further comprising:
    means for saturating said received sample with a first pressurized fluid.

13. The apparatus as defined by claim 12, further comprising:
    means for flushing said first pressurized fluid from said received sample and replacing said first fluid with a second pressurized fluid.

* * * * *